US008330082B2

(12) United States Patent
Hadfield

(10) Patent No.: US 8,330,082 B2
(45) Date of Patent: Dec. 11, 2012

(54) WARMING APPARATUS FOR CONTACT LENSES

(75) Inventor: Matthew David Hadfield, Dunlop (AU)

(73) Assignee: Qirx Pty Ltd. (AU)

( * ) Notice: Subject to any disclaimer, the term of this patent is extended or adjusted under 35 U.S.C. 154(b) by 249 days.

(21) Appl. No.: 12/600,387

(22) PCT Filed: May 15, 2008

(86) PCT No.: PCT/AU2008/000684
§ 371 (c)(1),
(2), (4) Date: May 14, 2010

(87) PCT Pub. No.: WO2008/141365
PCT Pub. Date: Nov. 27, 2008

(65) Prior Publication Data
US 2010/0258551 A1    Oct. 14, 2010

(30) Foreign Application Priority Data
May 18, 2007    (AU) ................ 2007902673

(51) Int. Cl.
*F27D 11/00*    (2006.01)
*H05B 3/06*    (2006.01)
(52) U.S. Cl. .......................... 219/428; 219/521
(58) Field of Classification Search .......... None
See application file for complete search history.

(56) References Cited

U.S. PATENT DOCUMENTS

| | | | |
|---|---|---|---|
| 3,801,278 A * | 4/1974 | Wagner et al. ............. 422/116 |
| 4,044,226 A | 8/1977 | Kadlecik et al. | |
| 4,228,136 A * | 10/1980 | Thomas ..................... 422/307 |
| 4,235,842 A * | 11/1980 | Thomas et al. ............. 422/116 |
| 4,242,572 A * | 12/1980 | Thomas et al. ............. 219/521 |
| 4,302,664 A * | 11/1981 | Ryder et al. ................ 219/504 |
| 4,307,289 A | 12/1981 | Thomas et al. | |
| 4,329,568 A | 5/1982 | Rocher et al. | |
| 4,341,948 A | 7/1982 | Sundstrom et al. | |
| 4,369,355 A | 1/1983 | Helixon | |
| 4,379,965 A | 4/1983 | Dounce et al. | |
| 4,388,521 A | 6/1983 | Thomas et al. | |

(Continued)

FOREIGN PATENT DOCUMENTS
AU    321397    10/2008
(Continued)

OTHER PUBLICATIONS

"U.S. Appl. No. 29/328,602, Non-Final Office Action mailed May 24, 2010", 6 pgs.

(Continued)

*Primary Examiner* — Scott B Geyer
(74) *Attorney, Agent, or Firm* — Schwegman Lundberg & Woessner, P.A.

(57) ABSTRACT

Disclosed is a contact lens warming apparatus (100) adapted to warm a contact lens (109) stored in a removably inserted lens container (102), the apparatus comprising a controller (106), a heatable cavity (103) shaped to be conformal to a corresponding contact surface (108) of the inserted lens container (102), said conformal contact surface facilitating the rapid repeatable warming of the contact lens (109), and a heating element (107), wherein the controller (106) is adapted to direct the heating element (107) to warm the inserted lens container (102) thereby warming the contact lens (109) in the lens container (102) in order to reduce discomfort otherwise felt by a wearer of the contact lens (109) when inserting the unwarmed contact lens (109) into their eye.

7 Claims, 11 Drawing Sheets

U.S. PATENT DOCUMENTS

| | | | |
|---|---|---|---|
| 4,441,769 A * | 4/1984 | Thomas et al. ............ 312/270.1 |
| 4,472,623 A | 9/1984 | Futter |
| 4,529,868 A | 7/1985 | Bowen et al. |
| D281,812 S | 12/1985 | Franczak et al. |
| D282,576 S | 2/1986 | Hoogesteger |
| 4,576,798 A * | 3/1986 | Hall et al. .................... 422/105 |
| D285,774 S | 9/1986 | MacLaughlin |
| D289,923 S | 5/1987 | Hoogesteger |
| 4,677,280 A * | 6/1987 | Kai .............................. 219/385 |
| 4,697,070 A | 9/1987 | Kai |
| 4,701,597 A | 10/1987 | Braun et al. |
| 4,743,738 A | 5/1988 | Ryder et al. |
| 4,823,944 A * | 4/1989 | Ryder .......................... 206/5.1 |
| 4,858,754 A | 8/1989 | Wright et al. |
| 4,863,698 A * | 9/1989 | Ryder et al. ................. 422/116 |
| 4,873,424 A * | 10/1989 | Ryder et al. ................. 219/521 |
| D320,278 S | 9/1991 | Ryder et al. |
| 5,111,029 A | 5/1992 | Grambush et al. |
| 5,126,538 A | 6/1992 | Kanner et al. |
| 5,129,999 A * | 7/1992 | Holland et al. .............. 205/701 |
| 5,452,792 A | 9/1995 | Zautke et al. |
| 6,318,548 B1 | 11/2001 | Travis |
| 6,362,460 B1 | 3/2002 | Fraker |
| D498,590 S | 11/2004 | Borovsky |
| 6,870,137 B1 * | 3/2005 | Clapp .......................... 219/433 |
| D512,565 S | 12/2005 | Sasso |
| D575,955 S | 9/2008 | Maraia et al. |
| 2007/0170075 A1 | 7/2007 | Winters et al. |
| 2007/0261970 A1 | 11/2007 | Stull |
| 2008/0272009 A1 | 11/2008 | Coon |

FOREIGN PATENT DOCUMENTS

| | | |
|---|---|---|
| AU | 322923 | 12/2008 |
| AU | 323912 | 1/2009 |
| EP | 0021828 | 1/1981 |
| JP | 4-073063 | 3/1992 |
| JP | 4-73063 A | 3/1992 |
| WO | WO-03074093 A2 | 9/2003 |
| WO | WO-2008/141365 A1 | 11/2008 |

OTHER PUBLICATIONS

"European Application No. 08747954.9, Extended European Search Report issued Oct. 1, 2010", 5 pgs.

"International Application Serial No. PCT/AU2008/000684, International Preliminary Report on Patentability and Written Opinion mailed Nov. 24, 2009", 6 pgs.

"Deluxe Laboratory Heater/Hotplate", onlinesciencemall.com, (Jun. 3, 2007), 1 pg.

"Laboratory Heating Plate", *Product Description by UVP*—file://P:\OPER\RAB\clients\anu%20connect%20ventures\heating%20plate.htm, (Jun. 26, 2006), 1 pg.

Shellock, Frank G., et al., "Increased Corneal Temperature Caused by MR Imaging of the Eye with a Dedicated Local Coil", *Radiology 1992*; No. 3, 185:697-699, (1992), 697-699.

"PCT Application Serial No. PCT/AU2008/000684, International Search Report mailed Aug. 27, 2008", 3 pgs.

"International Application No. PCT/AU2012/000433, International Search Report and Written Opinion mailed Jun. 1, 2012", 4 pgs.

* cited by examiner

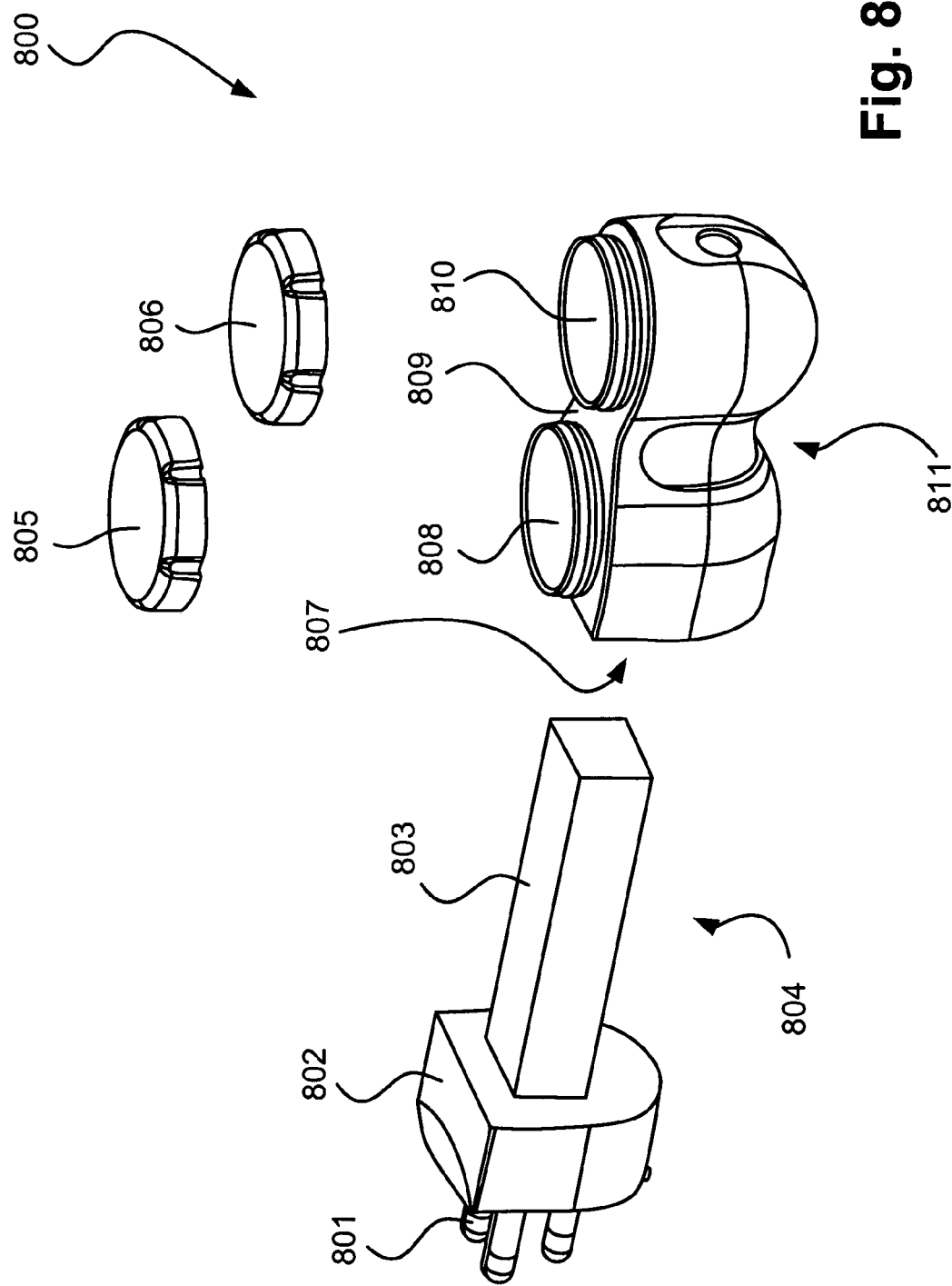

WARMING APPARATUS FOR CONTACT LENSES

PRIORITY CLAIM TO RELATED APPLICATIONS

This application is a national stage application under 35 U.S.C. §371 of PCT/AU2008/000684, filed May 15, 2008, and published as WO 2008/141365 A1 on Nov. 27, 2008, which claims priority to Australian Application No. 2007902673, filed May 18, 2007, which applications and publication are incorporated herein by reference and made a part hereof in their entirety, and the benefit of priority is claimed thereto.

FIELD OF THE INVENTION

The present invention relates generally to contact lenses, and in particular, to an apparatus for reducing discomfort associated with using contact lenses.

BACKGROUND

Contact eye lenses (hereinafter referred to simply as lenses) are becoming increasingly widespread. Unlike conventional spectacles, lenses are placed directly upon the surface of the wearer's eyes, which are both delicate and sensitive. The terms "placement upon the surface of the eyes" and "insertion into the eyes" are used interchangeably in this description. For both feelings of general wellbeing, and for reasons of safety, it is desirable to minimise any discomfort experienced by the wearer of the lenses, particularly when inserting the lenses into the eyes, in order to avoid the wearer flinching, and possibly injuring themselves as a result.

SUMMARY

It is an object of the present invention to ameliorate some of the discomfort sometimes experienced by users of contact lenses.

Disclosed are arrangements, referred to as tailored lens warming arrangements (or TLWA's) that gently warm the contact lens prior to insertion into the wearer's eye, to thus reduce the discomfort otherwise often experienced by the wearer when inserting an unwarmed lens into their eye.

According to a first aspect of the present invention, there is provided a contact lens warming apparatus adapted to warm a contact lens stored in a removably inserted lens container, the apparatus comprising:
  a controller;
  a heatable cavity shaped to be conformal to a corresponding contact surface of the inserted lens container, said conformal contact surface facilitating the rapid repeatable warming of the contact lens; and
  a heating element; wherein
the controller is adapted to direct the heating element to warm the inserted lens container thereby warming the contact lens in the lens container in order to reduce discomfort otherwise felt by a wearer of the contact lens when inserting the unwarmed contact lens into their eye According to another aspect of the present invention, there is provided a contact lens warming apparatus adapted to warm a contact lens stored in an integral lens container the apparatus comprising:
  a controller;
  the integral lens container; and
  a heating element; wherein
  the controller is adapted to direct the heating element to warm the lens container thereby warming the contact lens in the lens container in order to reduce discomfort otherwise felt by a wearer of the contact lens when inserting the unwarmed lens into their eye.

Other aspects of the invention are also disclosed.

BRIEF DESCRIPTION OF THE DRAWINGS

One or more embodiments of the present invention will now be described with reference to the drawings and appendices, in which:

FIG. 8 shows a mechanical representation of another example of a two-component TLWA; and APPENDIX A set out a pseudo-code implementation of the flow chart of FIG. 6.

DETAILED DESCRIPTION INCLUDING BEST MODE

Figure 1:
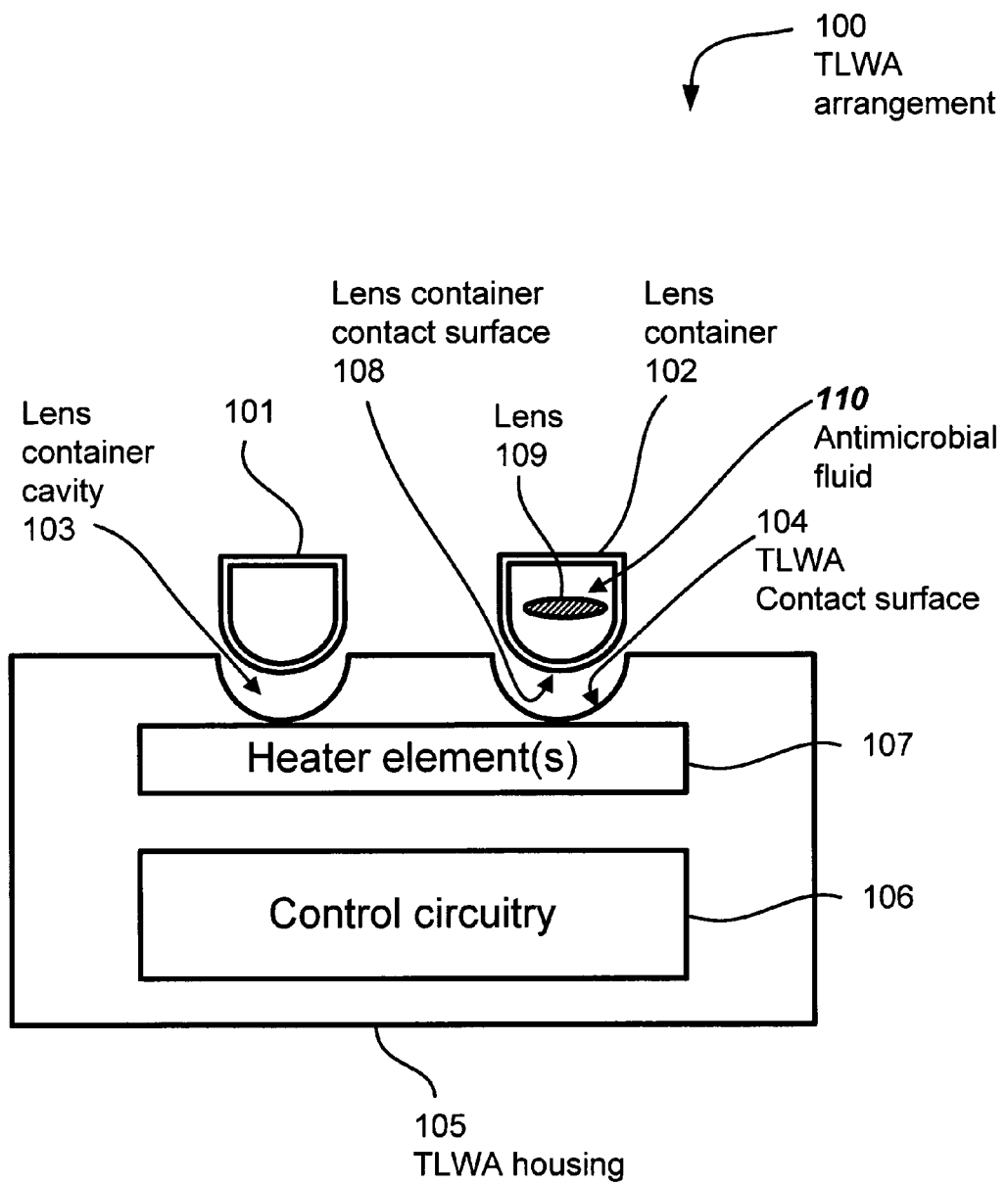
FIG. 1 shows a mechanical representation of one example of a single-component TLWA.

Where reference is made in any one or more of the accompanying drawings to features which have the same reference numerals, those features have for the purposes of this description the same function(s) or operation(s), unless the contrary intention appears.

It has been concluded that one of the possible sources of discomfort felt by users when inserting lenses into their eyes arises from the differential temperature between the lenses and the surface of the user's eyes. In one arrangement, the disclosed tailored lens warming arrangements (or TLWA's) warm the contact lens to within a specified temperature range that is preferably dependent upon the temperature of the exposed surface of the user's eye, this range being typically specified about a target temperature. This warming action, gently warming the lenses to the comfortable target range, preferably avoids inappropriate heating of the lens or the fluid in which the lens is stored, which could otherwise damage the lenses and/or compromise the antimicrobial capability of the fluid and/or damage the user's eyes.

The warming can be performed by applying a specified warming cycle, using a special-purpose lens warming apparatus, to the containers in which lenses are typically stored in an antimicrobial fluid. This is done prior to insertion of the lenses into the wearer's eyes. This brings the lenses from an initial temperature (typically down to 16° C. or lower depending on the ambient climatic temperature and domicile heating/insulation arrangements, and whether the lenses are stored in a refrigerator to reduce the growth of bacteria in the fluid) to within the specified temperature range, this being specified about the target temperature. The specified temperature range is preferably dependent upon the temperature of the exposed surface of the eye which is several degrees below body temperature (nominally 36.8° C.), and possibly also dependent upon the ambient temperature.

The warming cycle can ensure, if desired, in bringing the lenses to the specified temperature range, (a) that during a "warm-up mode" the temperature of the lenses and the antimicrobial fluid in which the lenses are stored remain within a rated specified temperature range, and/or (b) that during the warm-up mode neither the lenses being warmed, nor any part of the TLWA apparatus, exceed a specified maximum temperature, thus avoiding possible injury or discomfort to the user.

In one arrangement, the TLWA is used with removably insertable lens containers. In regard to this arrangement, there can be a number of different types and shapes of lens container. Repeatability and speed of the warming cycle in this arrangement can be facilitated by incorporating into the TLWA a heatable cavity shaped to be conformal to a corresponding contact surface of the particular lens container in question. This arrangement provides repeatable intimate contact over a substantial portion of the lens container between the heatable surface of the TLWA and the inserted mated lens container.

This intimate contact over a substantial contact area between the TLWA apparatus and the mated insertable lens container enables reliable rapid and repeatable warming of the lenses. The associated warming cycle can take into account the thermal inertia of the lens containers, the heat transfer characteristics of the conformal interface between the TLWA apparatus and the inserted lens container, the size and mass of the lens container, the amount of antimicrobial fluid in the container, the mass of the lenses and so on. The parameters associated with the warming cycle can be determined empirically, or analytically.

Having regard to the variety of lens containers on the market, a corresponding variety of TLWA devices can thus be provided in order to provide the above-noted conformal interface between a given type of lens container and the corresponding warming apparatus. Each particular TLWA device can thus be tailored to provide the required conformal interface between the TLWA apparatus and the corresponding type of lens container.

In an alternate arrangement, the lens container is not removably insertable into the TLWA, but it instead an integral part of the TLWA.

In yet another alternate arrangement, instead of providing a variety of TLWA devices in order to provide the conformal interfaces for different corresponding lens containers, a two-component TLWA apparatus can be used. In this arrangement one component of the TLWA apparatus is a heater module, and the other component is a shell which can accommodate a particular type of lens container. The shell can be mated to the heater module thus enabling operation of the TLWA apparatus as previously described. According to this arrangement, a user who wishes to change the type of contact lens they use (and hence to typically change the shape of the lens container) can purchase a suitable shell for use with their current heater module, rather than acquire an entirely new TLWA device. This type of arrangement can be used either in regard to insertably removable lens containers, or in regard to integral lens containers.

The TLWA approach makes the lenses more comfortable to insert into the wearer's eyes, thus preserving the wearer's comfort level, and possibly reducing the likelihood of injury by reducing the likelihood that the wearer will flinch when inserting an unwarmed lens into their eye. The TLWA approach can also help to ensure that the lenses and the antimicrobial fluid in which the lenses are stored in the lens containers remain within their specified operating temperature range, thus also helping to maintain antimicrobial capability of the lenses until they are removed from the lens containers.

The TLWA approach enables lens containers to be stored in a refrigerator, and the lenses to then be inserted into the user's eyes, without the discomfort that would otherwise arise from the differential temperature between the cooled lenses and the user's eye surfaces. Lenses can be stored in this manner to reduce growth of bacteria in the antimicrobial fluid in which the lenses are immersed in the lens containers.

FIG. 1 shows a mechanical representation 100 of one example of a TLWA. The TLWA in this example comprises a housing 105 containing one or more heating elements 107 that are controlled by control circuitry 106, this also being referred to as a controller. In the described arrangement, contact lenses such as 109 are each sealed in a lens container 102 that typically contains 5-10 ml of antimicrobial fluid 110. The TLWA housing 105 has lens cavities such as 103 each having a heatable contact surface 104 that is shaped to be conformal to a corresponding lens container contact surface 108. The cavities are referred to as heatable cavities. The intimate thermal contact (i.e. mating) that is thus achieved between the conformal TLWA contact surface 104 and the lens container contact surface 108 when the lens container 102 is removably inserted (meaning that the lens container can be inserted into the cavity, and then removed) into the lens container cavity 103 enables the heating elements 107 to rapidly, accurately and repeatably deliver the desired temperature/time warming profile. This profile ensures that the lens 109 is brought to within a specified temperature range about a desired target temperature. This is preferably achieved within a specified time interval. The TLWA arrangement also preferably maintains the lenses, after they have been warmed to the specified temperature range, within that range for a further specified time interval.

In one arrangement, the target temperature is specified to be 34° C. The specified temperature range about the target temperature can be specified as +/−2° C. about the target temperature or if circumstances so dictate, a greater range can be specified. In this arrangement, the specified time interval to reach the specified temperature range is 2 minutes+/−30 seconds. In this arrangement, during the warm-up mode, the TLWA ensures that neither the temperature of the TLWA apparatus nor any parts thereof, nor that of the lens container 102 or the lens 109 contained therein, overshoots (i.e. exceeds) a specified maximum temperature of 65° C. The specified time interval to maintain the temperature at the specified temperature range about the target temperature is 5 minutes+/−2 minutes.

The lens container 102 can take different forms within the aforementioned description, to accommodate use with either one-time use disposable lenses or use with re-usable lenses.

Figure 7:
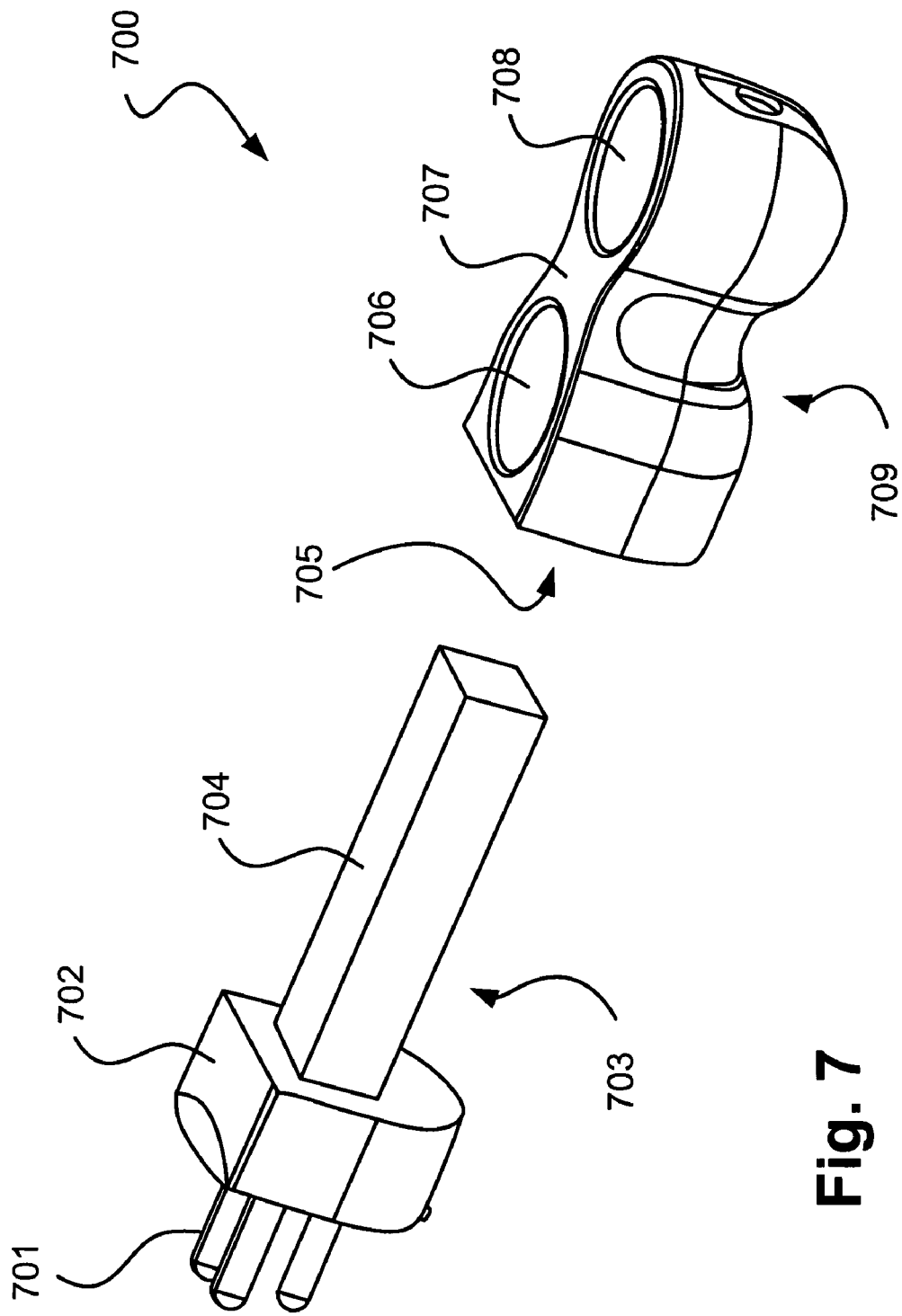
FIG. 7 shows a mechanical representation of an example of a two-component TLWA.

Different configurations of lens container 102 can be accommodated either (a) by providing associated TLWA devices with correspondingly configured conformal lens container cavities 103, or (b) by providing associated TLWA shells with correspondingly configured conformal lens container cavities, these shells being usable with a heater module (see FIG. 7 for more details). This "tailoring" of the TLWA cavities 103 to the lens containers 102 ensures intimate mating between the conformal TLWA contact surface 104 and the lens container contact surface 108 thus enabling the TLWA to operate in a repeatable manner irrespective of the particular configuration of the lens container 102. The lens wearer thus is able to use a TLWA device that is tailored to the particular configuration of lens container that he or she prefers.

Figure 2:
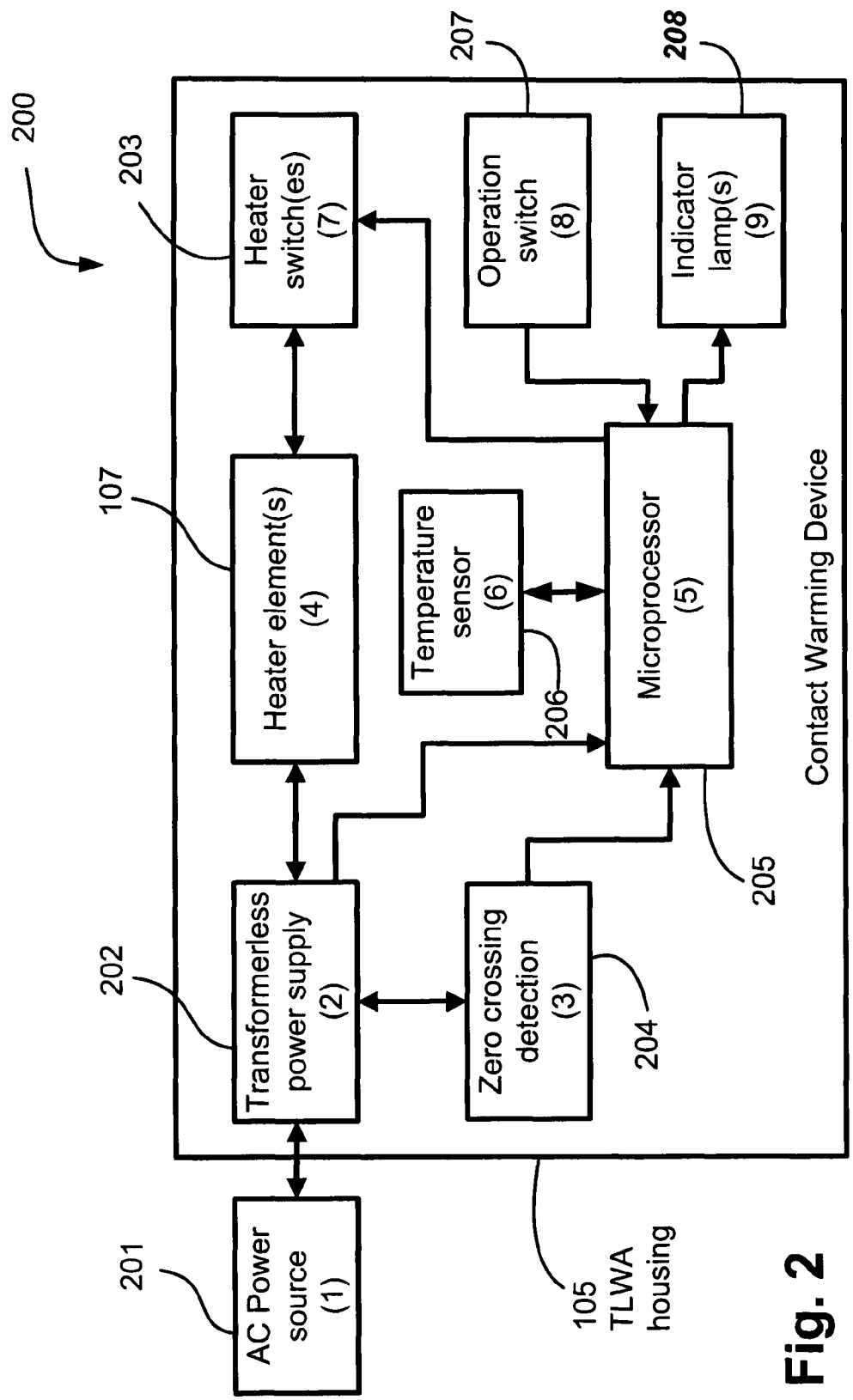
FIG. 2 shows an electrical (control) representation of the TLWA of FIG. 1.

FIG. 2 shows an electrical (control and heating) representation 200 of the TLWA of FIG. 1. The TLWA 200 comprises the following components in the present example:
An external AC power source 201;
a transformerless power supply 202;
a zero-crossing detector 204;
a heater element 107;
a micro controller 205;
a temperature sensor 206;
a heater switch 203;
a system operating switch 207; and
indicating lamps 208.

Power is supplied from the power source 201, via an AC electrical wall socket. The transformerless power supply parasitically taps a portion of the AC current provided by the AC power source 201 and converts it into a 5V DC power supply for the operation of the microprocessor 205, the temperature sensor 206, the heater switch 203, and the indicator lamps 208. The supply is "parasitic" in the sense that only a small amount of power (approximately $\frac{1}{1000}^{th}$ of power normally available from the wall socket) is required for the control electronics and is derived from the main AC power supply. The zero crossing detector 204 detects the zero crossing point of the AC current in the main AC power supply and this zero crossing point is used to time the operation of the heater switches 203 in order to minimise the electrical noise associated with the operation of the heater switches 203. The heater elements 107 are controlled, via the heater switches 203, by the micro-controller 205. The temperature sensor 206 monitors the temperature of the interface between the TLWA contact surface 104 and the lens container contact surface 108 and provides a feedback signal to the micro-controller 205. The operating switch 207 enables an external input from the user to be used to switch the TLWA 200 from an inactive to an active state. The indicating lamps 208 indicate the state of operation of the TLWA device 200.

When the TLWA device 200 is activated via the operating switch 207, in one arrangement the temperature of the heating elements 107 temperature is raised to a preset temperature for the period necessary to overcome the thermal inertia of the TLWA device 200 and the lens container 102 containing the contact lens 109. Once the aforementioned thermal inertia is overcome, the temperature sensor 206 is employed to monitor the TLWA device temperature at the interface between the TLWA contact surface 104 and the lens container contact surface 108. The temperature sensor 206 provides feedback to the micro-controller 205 so that the micro-controller 205 can control the heater elements 107 to bring the temperature of the contact lens container 102 to within the specified temperature range.

As previously noted, various warming profiles can be used, controlled by various control algorithms, provided that the desired temperature/time profile is satisfied. Thus, for example, on-off, proportional, proportional-integral-derivative (PID) or other control algorithm making use of the temperature sensor throughout the entire warm-up mode (see below) can be used.

Although the temperature sensor 206 in the described arrangement monitors the TLWA device temperature at the interface between the TLWA contact surface 104 and the lens container contact surface 108, other sensor arrangements can be used provided that the required temperature/time profile is satisfied. Thus, for example, an alternate arrangement can utilize one or more temperature sensors that monitor the temperature of the heater elements. This temperature sensor arrangement in conjunction with an algorithm on the micro-controller can be used to extrapolate the temperature of the interface based on characterization of the heater elements, the TLWA case and the lens container.

The disclosed TLWA arrangements support 3 modes of operation:
1. Standby mode—in which the TLWA device is neither warming nor maintaining the temperature of the lens container 102 (the TLWA device being either completely disabled, or in a state where some components are operating in order to reduce the start-up time when the TLWA device enters the next mode);
2. Warm-up mode—in which the TLWA device is raising the temperature of the TLWA contact surface 104, and by extension, the temperature of the contact lens container 102 from storage temperature to within the specified temperature range, preferably within the specified time interval without overshooting the specified maximum temperature; and
3. Maintain temperature mode—in which the temperature of the TLWA contact surface 104 is monitored by the temperature sensor 206 and controlled in order to maintain the temperature of the lenses within the specified temperature range for the specified time interval. When the set period expires the device returns to standby mode.

When the system operation switch 207 is operated once, the TLWA device automatically cycles through the three above-noted operational modes in sequence. The operational state of the TLWA is indicated via the indicator lamp 208. The colour of the indicator lamp can be varied (using either a multi-coloured LED or multiple LED's for example) to indicate the state of the TLWA device.

Although FIG. 2 depicts one type of control arrangement, other arrangements can be used within the scope of the TLWA concept. Thus for example the TLWA apparatus can be configured as a "plug pack" which is plugged directly into the AC power socket. In this arrangement, the system operation switch 207 can be omitted, and the system can be activated by the insertion of the plug pack into the power socket, this automatically causing the TLWA apparatus to cycle through the operational modes described. In another arrangement, the AC power source 201 and the power rectifier 202 can be replaced by a DC power source and suitable voltage regulator respectively. Alternately, an internal battery can be incorporated into the TLWA device in addition to or in place of the external power arrangement, thus increasing the portability of the TLWA arrangement. Furthermore, the indication lamps 208 can be omitted, if desired, or replaced with LCD indicators.

Furthermore, as previously noted that the control algorithm used by the microcontroller 205 to control the heater switches 203 and consequently the heater elements 107 can be based upon on-off, proportional, PID or other control methodologies, provided that the desired time/temperature profile can be achieved.

Although the electrical arrangement depicted in FIG. 2 has been described with reference to the TLWA arrangement of FIG. 1, the arrangement in FIG. 2 can also be used with the TLWS arrangements depicted in FIGS. 4, 7 and 8.

Figure 3:
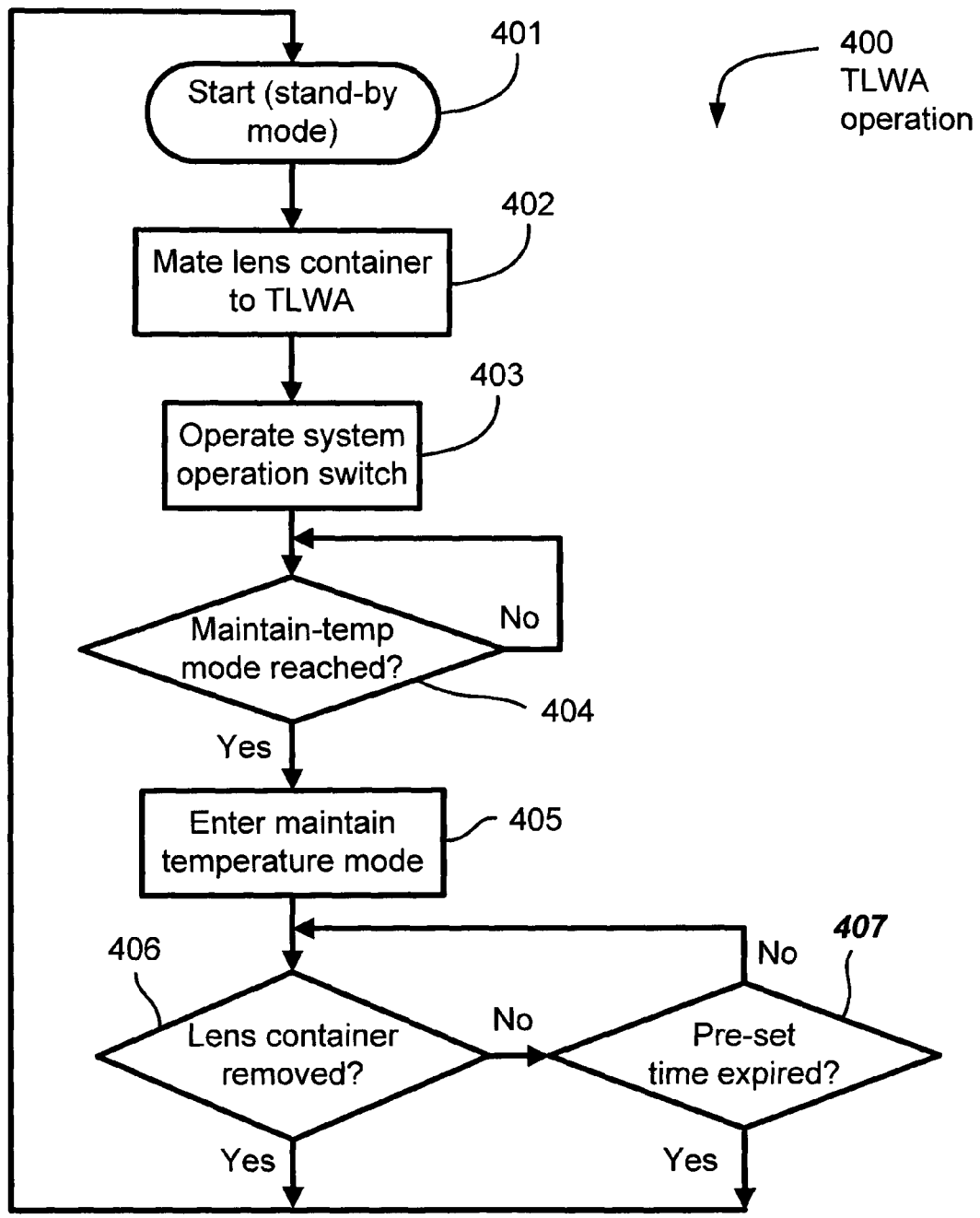
FIG. 3 shows a process of how the TLWA of FIG. 1 can be operated.

FIG. 3 shows a process 400 of how the disclosed TLWA device would typically be operated. In the example shown the process commences with a step 401 in which the TLWA device is in the "Stand-by mode". In a following step 402 the user removably inserts the lens container 102 to the TLWA device cavity 103 ensuring mating (i.e. conformal contact) between the lens container contact surface 108 and the TLWA contact surface 104. In a subsequent step 403 the user operates the system operation switch 207, thereby providing a system actuation signal initiating a device safety check, and subsequently initiating the "Warm-up mode". A subsequent decision step 404 determines if the TLWA device has reached the "Maintain temperature mode", as would be indicated by the lamp 208. If this is not the case, then the process 400 follows a NO arrow back to the step 404 in a looping fashion. If the step 404 indicates, according to the temperature sensor 206, that the lens container 102 has reached the "Maintain temperature mode" (this occurring when the lens container reaches the specified temperature range), then the process 400 follows a YES arrow to a step 405 in which the micro-controller 205 switches the TLWA device into the "Maintain temperature mode".

A following step 406 determines whether the lens container 102 has been removed from the lens container cavity 103 by sensing a slight change in the temperature of the interface between the lens container and the TLWA apparatus. If this is not the case, then the process follows a NO arrow to a step 407. The step 406 is optional and may be omitted as desired in alternate implementations. The step 407 determines if a pre-determined maintenance time interval has expired If this is not the case, then the process 400 follows a NO arrow back to the step 406. As noted, when the user removes the lens container 102 from the cavity 103, the temperature sensor 206 detects a temperature change, the step 406 returns a logical TRUE, and the process 400 follows a YES arrow according to which the micro-controller 205 returns the TLWA device to the "Standby-mode" in the step 401.

Returning to the step 407 for a functional description thereof, if the user does not remove the lens container 102 from the container cavity 103, the TLWA device maintains the temperature of the lens container 102 within the specified temperature range until the preset timer in the micro controller 205 has expired, in which event the micro-controller 205 returns the process 400 to the step 401 which places the TLWA device in the "stand-by mode". The maintenance period of 5 minutes can be varied, having regard to the fact that bacteria can begin to grow in the fluid in the lens container if this time becomes extended. The described arrangement allows a window of opportunity defined by the specified maintenance time for the user to remove the container 102, and if such does not occur, the TLWA device then shuts down to save power.

Although the process 400 in FIG. 3 has been described with reference to the TLWA arrangement of FIG. 1, it can also be used with the TLWS arrangement depicted in FIG. 7. The steps 403-405 in the process 400 apply to the TLWA arrangements depicted in FIGS. 4 and 8. These TLWA arrangements can, in a step similar to the step 406, detect when the lenses are removed from the respective integrally formed lens containers, after which the TLWA arrangements re-enter stand-by mode after expiration of a suitable pre-set time interval.

Figure 4:
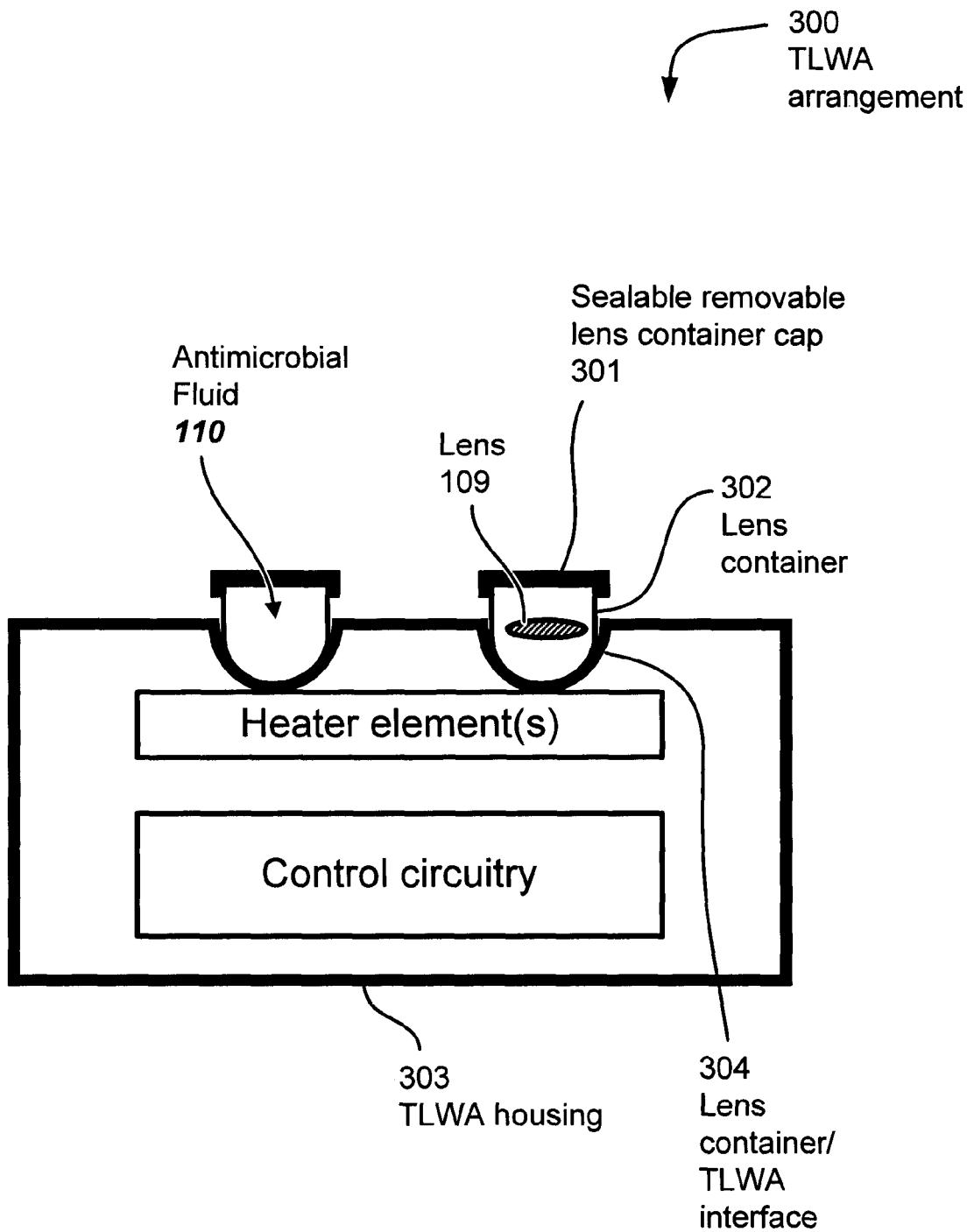
FIG. 4 shows a mechanical representation of another example of a single-component TLWA.
Figure 5A:
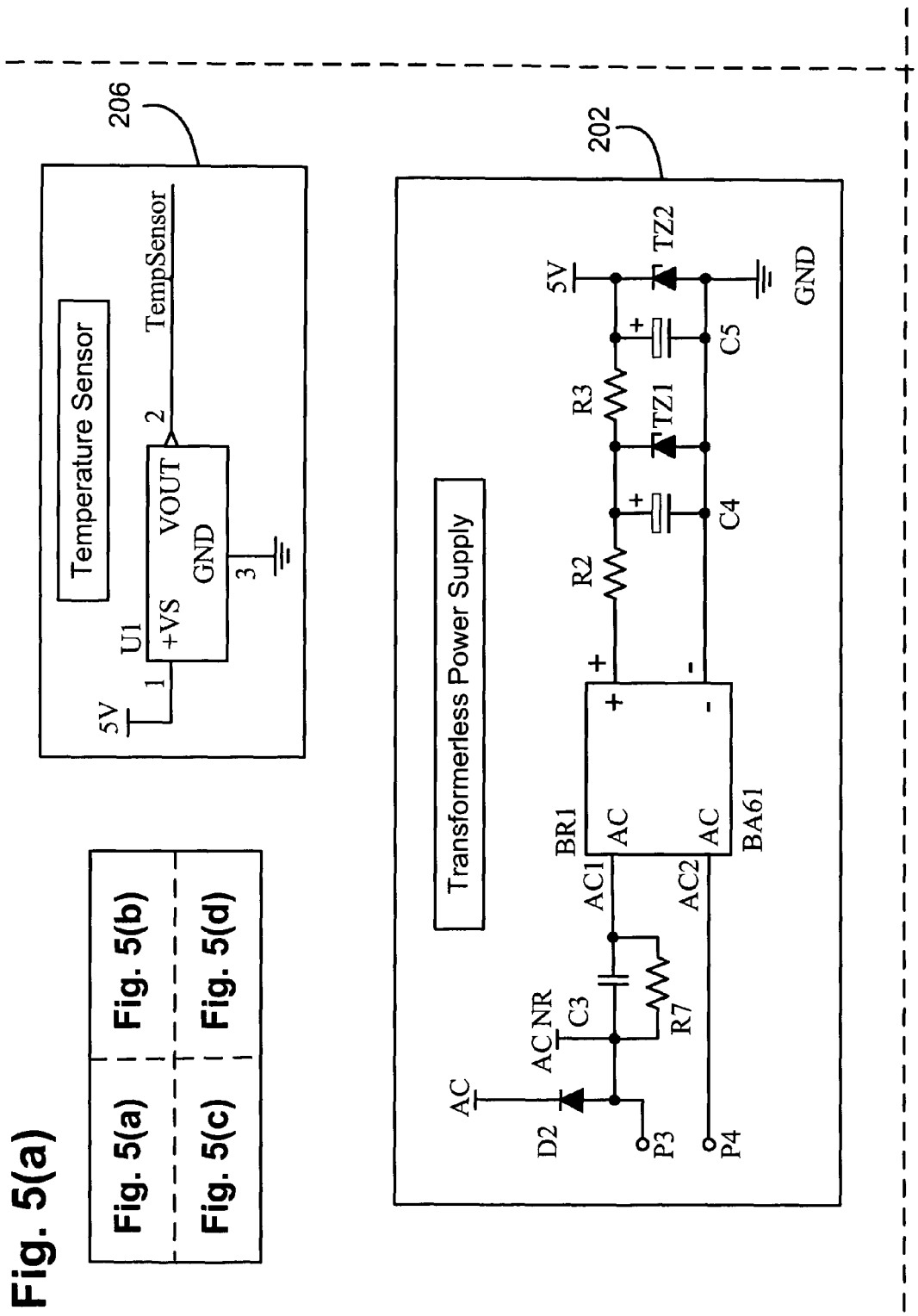
FIG. 5 shows one example of a schematic diagram for the electrical (control and heating) aspects of the TLWA of FIG. 1.
Figure 5B:
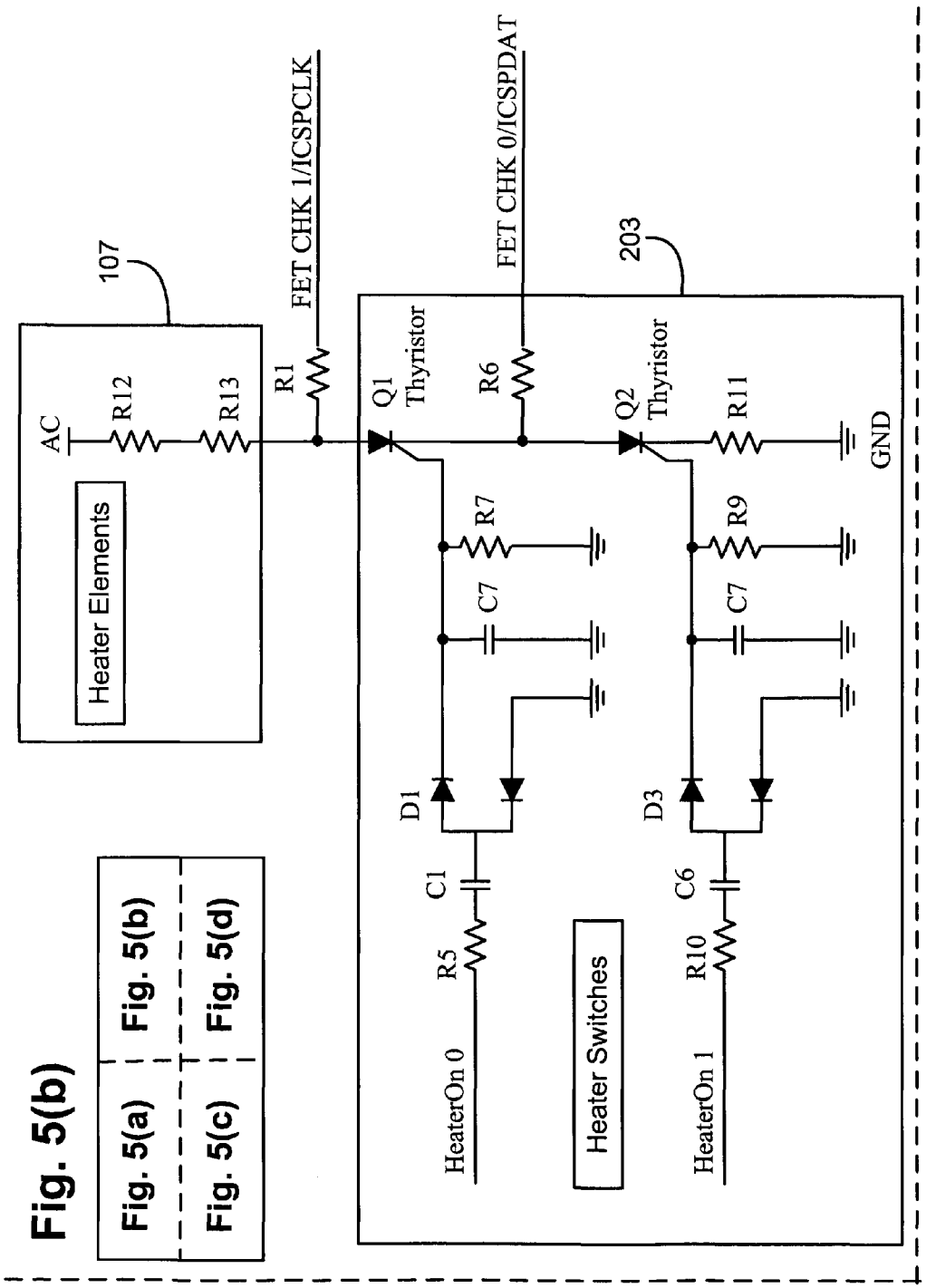
Figure 5C:
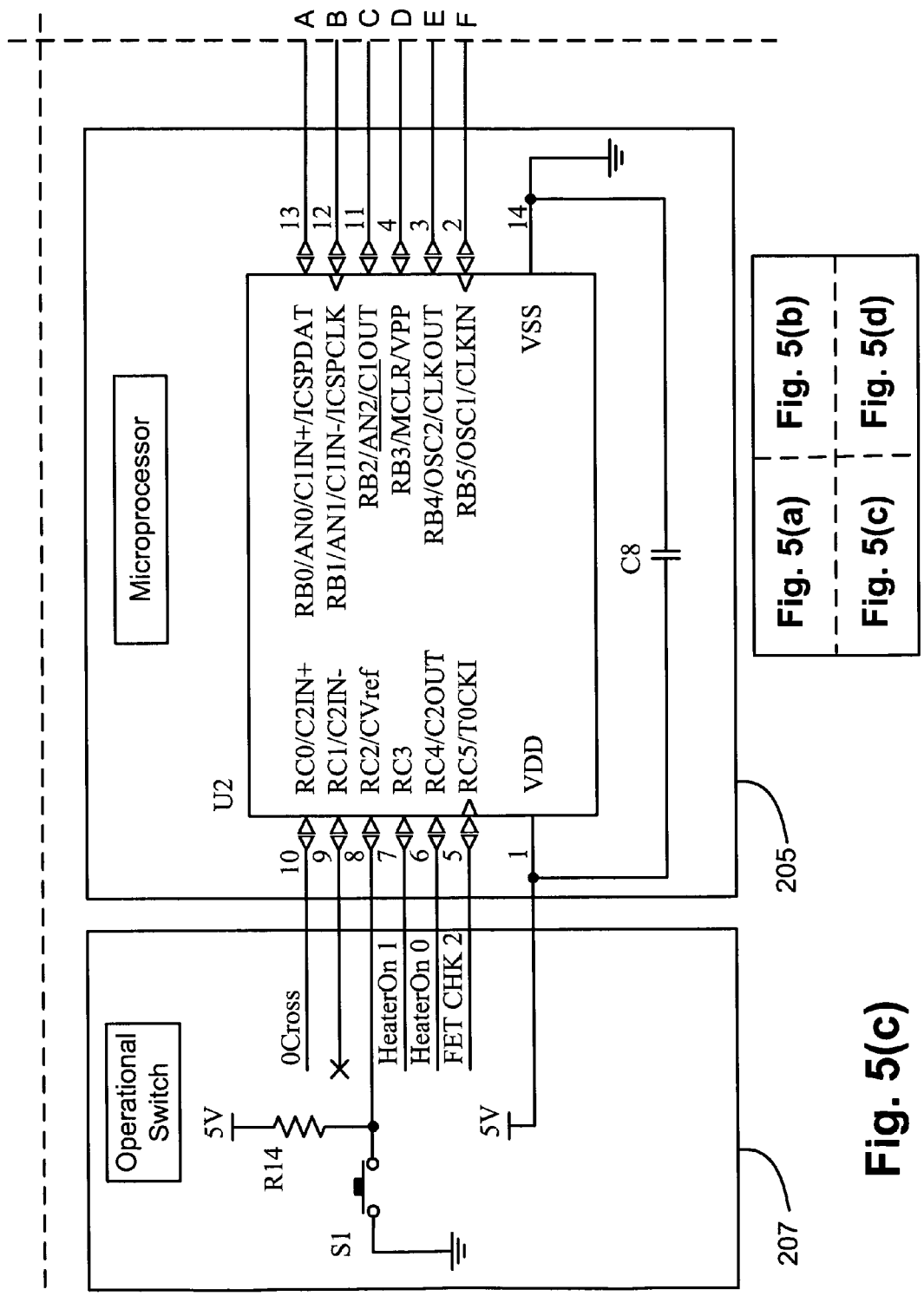
Figure 5D:
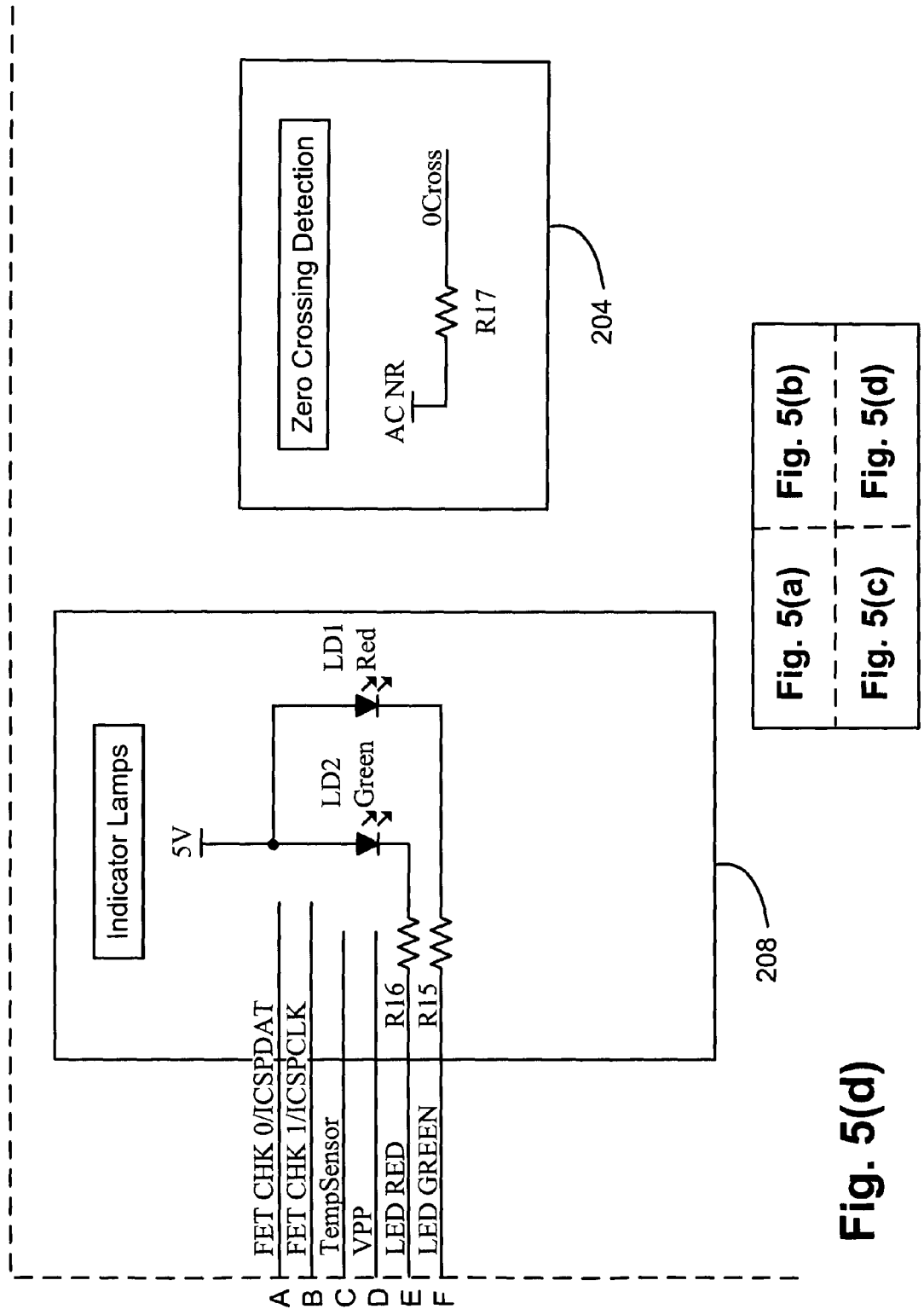

FIG. 4 shows a mechanical representation 300 of another example of the TLWA. In this arrangement a lens container 302 is an integral (non-removable) part of the TLWA housing 303. Accordingly, in one arrangement the container 302 can be formed as a cavity in the housing 303 with an integral collar projecting from the housing to enable the cap 301 to be fitted to the resultant "container". In another arrangement, the container can be formed by inserting a separate container in a non-removable fashion into a cavity in the housing, eg by press-fitting, or moulding, the container so that it becomes "integral" with the housing. The lens container in this example has a sealable removable cap 301 which is removed in order to remove the lens 109 from the container 302. According to the second arrangement noted above, the mating between the (separate) lens container 302 and the TLWA device is permanent, and forms a permanent lens container/TLWA interface 304.

Operation of the TLWA device in FIG. 4 is similar to that of the arrangement in FIG. 1 except that there are additional steps for maintaining the antimicrobial capability of the contact lens whilst it is in the TLWA device. Thus, for example, it would be necessary to clean the lens container 302 and the removable cap 301 using suitable cleaning materials between successive uses of the TLWA arrangement. The step 406 in FIG. 3 may be omitted in this arrangement if the change in mass is too small to be reliably detected.

FIG. 5 shows one example of a schematic diagram for the electrical (control) aspects of the TLWA of FIG. 1. Schematic sub-systems for the heater elements, heater switches, zero crossing detection, temperature sensor, transformerless power supply, operational switch, microprocessor and indicator lamps are designated by respective reference numerals 107, 203, 204, 206, 202, 207, 205 and 208 respectively.

Although the electrical arrangement depicted in FIG. 5 has been described with reference to the TLWA arrangement of FIG. 1, the arrangement in FIG. 5 can also be used with the TLWS arrangements depicted in FIGS. 4, 7 and 8.

Figure 6:
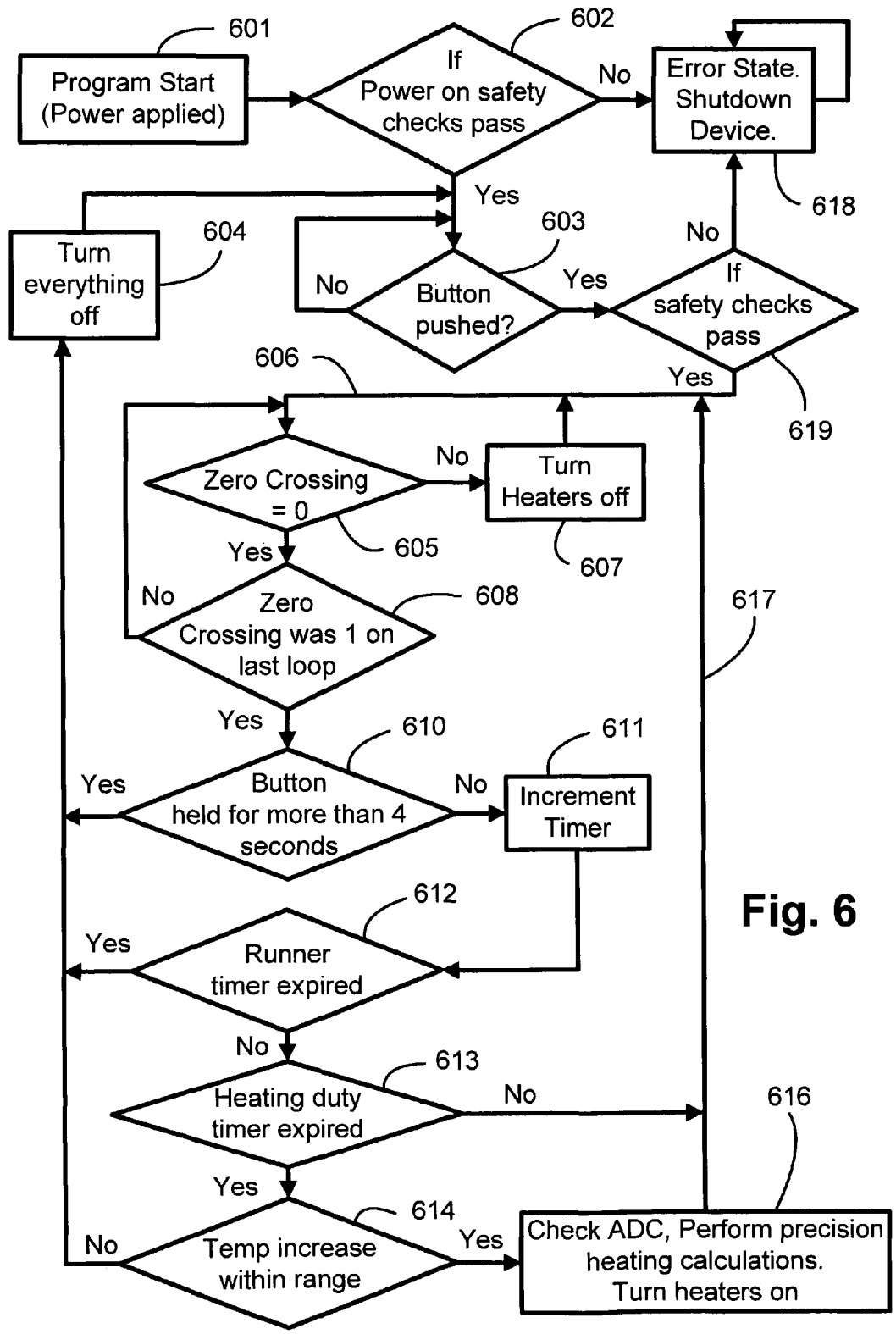
FIG. 6 shows one example of a flow chart depicting a process used by the TLWA of FIG. 1.

FIG. 6 shows one example of a flow chart depicting a process 600 that can be used by the TLWA controller. APPENDIX A set out a pseudo-code implementation of how the aforementioned process 600 can be implemented. The process 600 commences with a start step 601 in which power is supplied, after which a decision step 602 determines if the power safety check being conducted by the microprocessor 205 has been passed. If this is not the case then the process follows a NO arrow to a step 618, which constitutes an "error state" and the TLWA shuts down. If however the step 602 returns a logical TRUE, the process follows a YES arrow from the step 602 to a decision step 603. In the step 603 the microprocessor 205 determines if the button 207 has been activated. If this is not the case, then the process 600 follows a NO arrow back to the step 603 in a looping fashion.

If the step 603 returns a logical TRUE then the process follows a YES arrow to a decision step 619 which conducts a further determination of whether safety checks have been passed. If this is not the case, then the process 600 follows a NO arrow from the step 619 to the step 618. If however the step 619 returns a logical TRUE, then the process 600 follows a YES arrow from the step 619 to a decision step 605 in which the microprocessor 205 and the zero crossing detection module 204 determine if the zero crossing detection is a "0" (i.e. at approximately 0 volts). If this is not the case then the process follows a NO arrow to a step 607 in which the microprocessor 205 turns the heater elements 107 off using the heater switches 203. The process is then directed as depicted by an arrow 606 back to the step 605.

If the step 605 returns a logical TRUE then the process follows a YES arrow to a step 608 in which the microprocessor 205 and the zero detection module 204 determine if the zero crossing was "1" (i.e. greater than 0 volts) on the last loop. If this is the case, then the process follows a YES arrow to a step 610 in which the microprocessor 205 determines if the button 207 was held for more than 4 seconds. If this is the case, then the process follows a YES arrow to a step 604 in which the microprocessor 205 turns the TLWA off. The process if then directed by an arrow 615 to the step 603.

Returning to the step 608, if the step returns a logical FALSE, then the process follows a NO arrow to the step 605.

Returning to the step 610, if the step returns a logical FALSE, then the process follows a NO arrow to a step 611 in which the microprocessor 205 increments a timer relating to the maintenance time. In a following decision step 612 the microprocessor 205 determines if the timer has expired. If this is the case, then the process is directed by a YES arrow to the step 604.

Returning to the step 612, if the step returns a logical FALSE, then the process follows a NO arrow to a step 613 in which the microprocessor 205 determines if the warming duty timer has expired. If this is not the case, then the process follows a NO arrow back to the step 605. If however the step 613 returns a logical TRUE then the process follows a YES arrow to a step 614 in which the microprocessor 205 determines if the temperature increase is within range. The temperature range referred to here relates to the maximum allowable temperature, the maximum allowable rate of change in temperature for the entire system, and where the current temperature fits within these operational parameters. If this is not the case, then the process follows a NO arrow to the step 604. If however the step 614 returns a logical TRUE, then the process follows a YES arrow to a step 616 in which the microprocessor 205 checks the Analogue to Digital Conversion (ADC), performs precision warming calculations, turns the heating elements 107 on using the heating switches 203, and the process follows an arrow 617 back to the step 605.

FIG. 7 shows a mechanical representation of an example of a two-component TLWA. The TLWA in this example comprises a first component being a heater module 703, and a second component being a shell 709, these two components forming the two-component TLWA when thermally connected.

The depicted heater module 703 has three pins 701 which are adapted for insertion into a standard power socket. Clearly other pin arrangements can be used, such as two pin configurations which do not have an earth pin. The heater module 703 also has a housing 702 which can contain the electronic circuitry shown in FIG. 5. The heating element 704 extends from the housing 702 and is shaped for insertion, as depicted by an arrow 705, into a correspondingly shaped socket (not shown) in the shell 709.

The heater module and the shell are thermally connectable by shaping the heating element and the socket in a manner as to ensure snug contact (i.e. good thermal contact) between the heating element 704 and the shell 709 when the heating element is fully inserted into the socket. This full insertion also enables operation of the operational switch S1 at 207 (see FIG. 5) thereby providing a safety interlock which prevents the heater element 704 from heating up while outside the socket in the shell 709.

The shell 709 comprises a shell housing 707 and, in the example shown in FIG. 7, two lens container cavities 706 and 708 formed in the shell housing 707. These lens container cavities 706 and 708 are tailored to each have a heatable contact surface (such as 103 in FIG. 1) that is shaped to be conformal to a corresponding lens container contact surface (such as 108 in FIG. 1). This two-component arrangement enables a user to keep the heater module 703 and merely change the shell 709 if the user wishes to change the lens supplier and hence change the shape of the lens containers.

The shell 709 is typically made of a material whose thermal conduction properties facilitate heating of the lens containers (not shown) when inserted into the respective lens container cavities 706, 708.

Although the TLWA arrangement in FIG. 7 shows the heater module 703 adapted for insertion into a socket in the shell 709, other arrangements can be used to mate (i.e. thermally connect) the heater module and the shell in order to provide suitable thermal contact. Thus, for example, the heater module could consist of a flat heating plate 710 adapted for pressure mating against a corresponding flat surface (not shown) at 711 on the shell 709.

Furthermore, although the TLWA arrangement in FIG. 7 depicts a particular configuration of shell which completely envelops the heating element 704 when the shell 709 and the heating module 703 are thermally connected, other two-component TLWA arrangements can be used.

FIG. 8 shows a mechanical representation of another example of a two-component TLWA. The TLWA in this example comprises a heater module 804 and a shell 811. The depicted heater module 804 has three pins 801 which are adapted for insertion into a standard power socket. Other pin configurations, including two pin arrangements which do not include an earth pin, can also be used. The heater module 804 also has a housing 802 which can contain the electronic circuitry shown in FIG. 5. The heating element 803 extends from the housing 802 and is shaped for insertion, as depicted by an arrow 807, into a correspondingly shaped socket (not shown) in the shell 811.

The heating element and the socket are shaped in a manner as to ensure good thermal contact between the heating element 803 and the shell 811 when the heating element is fully inserted into the socket. This full insertion also enables operation of the operational switch S1 at 207 (see FIG. 5) thereby providing a safety interlock which prevents the heater element 803 from heating up while outside the socket in the shell 811.

The shell 709 comprises a shell housing 809 and, in the example shown in FIG. 8, two integrally formed lens cavities 808 and 810. These lens cavities 808 and 810 may be of any convenient shape for enabling contact lenses to be stored therein in a similar manner to that depicted in FIG. 4.

INDUSTRIAL APPLICABILITY

It is apparent from the above that the arrangements described are applicable to the domestic appliance and health equipment industries.

The foregoing describes only some embodiments of the present invention, and modifications and/or changes can be made thereto without departing from the scope and spirit of the invention, the embodiments being illustrative and not restrictive.

Accordingly, other temperature ranges and time intervals can be specified, in order to optimise the TLWA functionality in particular circumstances. These circumstances may depend, among other considerations, upon the prevailing ambient temperature, the age and possibly other demographic variables relating to the users and so on.

APPENDIX A

Example Pseudo Code

Function : pwr_freq_calb( )
Purpose: Determines the frequency of the power supply (currently only chooses between 50 and 60 Hz). Sets the variables PWR_OFF_CNST, ERROR_CODE_CNST and runs_timer according to the frequency of the power supply so that the behaviour of the device is independent of the power supply frequency.

APPENDIX A-continued

Example Pseudo Code

```
Input: none
Returns: none
Effects: Timing variables
Called by: The initialisation part of the main procedure
Synopsis:
Delay until the start of a power cycle
Clear the timer register
Delay until the power cycle has finished
Delay until the next power cycle starts
If the timer register is greater than a threshold it is 50 Hz (else 60 Hz)
Set variables accordingly
********************************************************************}
{********************************************************************
Function : delta_check( )
Purpose: Turns the unit off if there is a sudden increase, or if there is absolutely no
increase in temperature (caused by removing the lens holder, or a broken temp sensor,
respectively)
Input: none
Returns: none
Effects: previous_temp, can turn unit off
Called by: Called periodically during the main loop
Synopsis:
(Enter this routine periodically, but not on every power cycle)
Calculate difference (Delta) in temperature, compared to last measurement
If Temperature is significantly below set point, and Delta is 0,
Turn Unit off
If Temperature Delta is too large
Turn unit off
Move current temperature into previous temperature variable
********************************************************************}
{********************************************************************
Function: pwr_on_check( )
Purpose: To check the status of the thyristors before we apply mains power to the heating
elements. Unless both thyristors are activated, no current should pass through the heating
resistors; hence the test pin should read digital "0".
Input: none
Returns: bit (return 1 if there is a problem).
Effects: Test_var (records problems for debugging - if required)
Called by: The initialisation part of the main procedure
Synopsis
Clear error checking variables
For each state of the two thyristors (00, 01, 10, 11)
Wait until not a power cycle (we need the start of a power cycle)
Wait until a power cycle
Wait 2 milliseconds (to allow sufficient voltage for testing power components)
Toggle the low voltage output pins for heaters (if needed) for sufficient time
Check power circuit
Record problems in variables (if any)
Return the value of broken
(Note: errors are stored in test_var as different bits in a byte, so that multiple problems
can be
diagnosed)
********************************************************************}
{********************************************************************
Function: wait(int)
Purpose: To allow for an 'accurate' delay of a specified number of milliseconds
Input: An integer (***current;y signed, probably should be unsigned) between 0 and 127
Returns: none
Effects: none
Called by: various - pwr_on_chk, main
Synopsis
Set timer register to use required pre-scaler
Loop for the number of ms required
Clear timer
Wait for timer to reach threshold
********************************************************************}
{********************************************************************
Function: pulsethyristors ( )
Purpose: To pulse the thyristor "heart-beat monitor" circuit for long enough to allow the
thyristors time to open and latch. This function operates both thyristors.
Input: none
Returns: none
Effects: Heater output pins
Called by: Main
Synopsis
While not a power cycle
```

APPENDIX A-continued

Example Pseudo Code

Pulse Heater outputs (requires a certain time before thyristor will open)
For a specified period
Pulse Heater outputs (require a finite time to "latch" the thryistors)
**********************************************************************}
{**********************************************************************
Function: heater_state ( )
Purpose: Sets the duty cycle for the heater based on current temperature from the sensor.
Input: None
Returns: None
Effects: toohot, zero_cross_count. Reads adresult.
Called by: Main
Synopsis:
Case of adresult
< Cold then set cold_duty
< Nearly_Warm set Nearly_Warm Duty
< Warm set Warm duty
< Hot set Hot duty
> Hot turn off and delay for 5 seconds before trying again.
**********************************************************************}
{**********************************************************************
Function: ADC_Measure ( )
Purpose: Measures the voltage input on the ADC pin and converts it to a integer.
Input: None
Returns: None
Effects: adres
Called by: Main
Synopsis:
Set ADC read parameters.
Set AD_Convert flag
Loop until AD_Result flag set
Adresult = ADC value.
**********************************************************************}
{**********************************************************************
Function: portInit ( )
Purpose: Initialise all the IO ports, Option registers and comparator ports.
Input: None
Returns: None
Effects: TRISB, PORTB, TRISC, PORTC, OPTION, CM2CON0, CM1CON0
Called by: Main
Synopsis:
Set Registers with default values.
**********************************************************************}
{**********************************************************************
Function: Main ( )
Purpose: Controls the program.
Input: None
Returns: None
Effects: All variables
Called by: N/A
Synopsis
Call Initialisation routines
Initialise other outputs and variables
Call frequency calibration check (pwr_freq_calb)
Call power-on-self-test (pwr_on_chk)
If power-on-self test fails, and button pushed for 10 seconds
Display human-readable error code(s)
[Main loop]
Turn off heaters, lights and reset running-timer
If button is pushed
If button pushed for more than 4 seconds, turn unit off (return to main loop)
Else (if button pushed for less than 4 seconds) Enter running loop
[Running Loop]
If we are in a low power cycle
If we just finished a positive power cycle
Increment run timer and turn unit off if set-time is reached (Go to Main Loop)
Increment duty-counter
If duty-counter set-value is reached
Measure temperature (call ADC_Measure)
Determine which duty cycle to use, and set duty-counter (heater_state)
If temperature not over-range
Run a Heat cycle (Call puslethyristors)
Else leave heaters off.
Else Wait until next power cycle
Else go to Running loop
Else (If we are in a positive power cycle)
Turn all lights and heaters off go to Running Loop
**********************************************************************}

The invention claimed is:

1. A contact lens warming apparatus adapted to warm a contact lens stored in a removably inserted lens container, the apparatus comprising;
   a controller;
   a heatable cavity shaped to be conformal to a corresponding contact surface of the inserted lens container conformal contact surface facilitating the rapid repeatable warming of the contact lens; and
   a heating element; wherein
   the controller is adapted to direct the heating element to warm the inserted lens container, thereby warming the contact lens in the lens container in order to reduce discomfort otherwise felt by a wearer of the contact lens when inserting the unwarmed contact lens into their eye;
   said contact lens warming apparatus having a plurality of heatable cavities adapted to receive a corresponding plurality of lens containers;
   said contact lens warming apparatus further comprising a temperature sensor, wherein the controller is adapted to direct the heating element responsive to a signal from the temperature sensor to thereby warm the contact lens to within a specified temperature range; and
   wherein the specified temperature range is 34° C.+/−2° C.

2. A contact lens warming apparatus adapted to warm a contact lens stored in a removably inserted lens container, the apparatus comprising:
   a controller;
   a heatable cavity shaped to be conformal to a corresponding contact surface of the inserted lens container conformal contact surface facilitating the rapid repeatable warming of the contact lens; and
   a heating element; wherein
   the controller is adapted to direct the heating element to warm the inserted lens container, thereby warming the contact lens in the lens container in order to reduce discomfort otherwise felt by a wearer of the contact lens when inserting the unwarmed contact lens into their eye;
   said contact lens warming apparatus having a plurality of heatable cavities adapted to receive a corresponding plurality of lens containers;
   said contact lens warming apparatus further comprising a temperature sensor, wherein the controller is adapted to direct the heating element responsive to a signal from the temperature sensor to thereby warm the contact lens to within a specified temperature range;
   wherein the controller is further adapted to warm the contact lens to within the specified temperature range without the apparatus exceeding a maximum temperature; and
   wherein the maximum temperature is 65° C.

3. A contact lens warming apparatus adapted to warm a contact lens store in a removably inserted lens container, the apparatus comprising:
   a controller;
   a heatable cavity shaped to be conformal to a corresponding contact surface of the inserted lens container, said conformal contact surface facilitating the rapid repeatable warming of the contact lens; and
   a heating element; wherein
   the controller is adapted to direct the heating element to warm the inserted lens container, thereby warming the contact lens in the lens container in order to reduce discomfort otherwise felt by a wearer of the contact lens when inserting the unwarmed contact lens into their eye;
   said contact lens warming apparatus having a plurality of heatable cavities adapted to receive a corresponding plurality of lens containers;
   said contact lens warming apparatus further comprising a temperature sensor, wherein the controller is adapted to direct the heating element responsive to a signal from the temperature sensor to thereby warm the contact lens to within a specified temperature range;
   wherein the controller is further adapted to warm the contact lens to within the specified temperature range within a specified time interval; and
   wherein the specified time interval is 2 minutes+/−30 seconds.

4. A contact lens warming apparatus adapted to warm a contact lens stored in a removably inserted lens container, the apparatus comprising:
   a controller;
   a heatable cavity shaped to be conformal to a corresponding contact surface of the inserted lens container, said conformal contact surface facilitating the rapid repeatable warming of the contact lens; and
   a heating element; wherein
   the controller is adapted to direct the heating element to warm the inserted lens container, thereby warming the contact lens in the lens container in order to reduce discomfort otherwise felt by a wearer of the contact lens when inserting the unwarmed contact lens into their eye;
   said contact lens warming apparatus having a plurality of heatable cavities adapted to receive a corresponding plurality of lens containers;
   said contact lens warming apparatus further comprising a temperature sensor, wherein the controller is adapted to direct the heating element responsive to a signal from the temperature sensor to thereby warm the contact lens to within a specified temperature range;
   wherein the controller is further adapted to warm the contact lens to within the specified temperature range within a specified time interval; and
   wherein the controller is further adapted, after warming the contact lens to within the specified temperature range within the specified time interval, to maintain the contact lens within the specified temperature range for a further specified time interval.

5. The contact lens warming apparatus according to claim 4, wherein the further specified time interval is 5 minutes+/−2 minutes.

6. A contact lens warming apparatus adapted to warm a contact lens stored in a removably inserted lens container, the apparatus comprising:
   a controller;
   a heatable cavity shaped to be conformal to a corresponding contact surface of the inserted lens container, said conformal contact surface facilitating the rapid repeatable warming of the contact lens; and
   a heating element; wherein
   the controller is adapted to direct the heating element to warm the inserted lens, container, thereby warming the contact lens in the lens container in order to reduce discomfort otherwise felt by a wearer of the contact lens when inserting the unwarmed contact lens into their eye;
   said apparatus comprising two thermally connectable components, wherein:
   a first one of the two components includes the heatable cavity;

a second one of the two components includes the heating element; and the two components are adapted to be thermally connected, thereby enabling the heating element to warm the lens container inserted into the heatable cavity; and wherein the heating element in the second component is insertable into a socket in the first component, said insertion thermally connecting the first component and the second component.

7. The contact lens warming apparatus according to claim 6, wherein operation of the heating element is disabled unless the first component is thermally connected to the second component.

* * * * *

UNITED STATES PATENT AND TRADEMARK OFFICE
CERTIFICATE OF CORRECTION

PATENT NO. : 8,330,082 B2
APPLICATION NO. : 12/600387
DATED : December 11, 2012
INVENTOR(S) : Matthew David Hadfield Page 1 of 1

It is certified that error appears in the above-identified patent and that said Letters Patent is hereby corrected as shown below:

In the Claims

In column 15, line 4, in Claim 1, delete "comprising;" and insert --comprising:--, therefor In column 15, line 7, in Claim 1, delete "container" and insert --container, said--, therefor In column 15, line 31, in Claim 2, delete "container" and insert --container, said--, therefor In column 15, line 55, in Claim 3, delete "store" and insert --stored--, therefor In column 16, line 60, in Claim 6, delete "lens," and insert --lens--, therefor Signed and Sealed this
Fourteenth Day of May, 2013

Teresa Stanek Rea
*Acting Director of the United States Patent and Trademark Office*